United States Patent
Truppo et al.

(10) Patent No.: US 10,150,959 B2
(45) Date of Patent: Dec. 11, 2018

(54) IMMOBILIZED KETOREDUCTASES AND PROCESS FOR MAKING AND USING IMMOBILIZED KETOREDUCTASE

(71) Applicant: Merck Sharp & Dohme Corp., Rahway, NJ (US)

(72) Inventors: Matthew D. Truppo, Bradley Beach, NJ (US); Hongmei Li, Edison, NJ (US); Johannah R. Moncecchi, Jersey City, NJ (US); Hallena Strotman, Somerset, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 147 days.

(21) Appl. No.: 14/771,511

(22) PCT Filed: Mar. 12, 2014

(86) PCT No.: PCT/US2014/023844
§ 371 (c)(1),
(2) Date: Aug. 31, 2015

(87) PCT Pub. No.: WO2014/150633
PCT Pub. Date: Sep. 25, 2014

(65) Prior Publication Data
US 2016/0053251 A1 Feb. 25, 2016

Related U.S. Application Data

(60) Provisional application No. 61/898,503, filed on Nov. 1, 2013, provisional application No. 61/791,247, filed on Mar. 15, 2013.

(51) Int. Cl.
| | | |
|---|---|---|
| *C12N 9/04* | (2006.01) | |
| *C12N 11/08* | (2006.01) | |
| *C12P 7/02* | (2006.01) | |
| *C12P 7/22* | (2006.01) | |

(52) U.S. Cl.
CPC ............ *C12N 11/08* (2013.01); *C12N 9/0006* (2013.01); *C12P 7/02* (2013.01); *C12P 7/22* (2013.01)

(58) Field of Classification Search
CPC ......... C12N 11/08; C12N 9/0006; C12P 7/22; C12P 7/02
See application file for complete search history.

(56) References Cited

U.S. PATENT DOCUMENTS

| | | |
|---|---|---|
| 7,326,708 B2 | 2/2008 | Cypes et al. |
| 7,468,459 B2 | 12/2008 | Xiao et al. |
| 8,293,507 B2 | 10/2012 | Savile et al. |
| 2009/0275066 A1 | 11/2009 | Popot et al. |
| 2009/0286303 A1 | 11/2009 | Bowers et al. |
| 2010/0285541 A1 | 11/2010 | Saville et al. |
| 2011/0033391 A1 | 2/2011 | Weiner |

FOREIGN PATENT DOCUMENTS

| | | | |
|---|---|---|---|
| WO | WO2003068909 A2 | 8/2003 | |
| WO | WO2007133184 A2 | 11/2007 | |
| WO | WO2010025085 A2 | 3/2010 | |
| WO | WO2011005477 A1 | 1/2011 | |
| WO | WO2011017551 A1 | 2/2011 | |
| WO | WO2011100265 * | 8/2011 | |
| WO | WO2011100265 A2 | 8/2011 | |
| WO | WO-2012058134 A1 * | 5/2012 | ........... A61K 31/496 |
| WO | WO2012142302 A2 | 10/2012 | |
| WO | WO2012177527 A1 | 12/2012 | |
| WO | WO2013074650 * | 5/2013 | |
| WO | WO2013074650 A1 | 5/2013 | |
| WO | WO2014150633 A1 | 9/2014 | |

OTHER PUBLICATIONS

Musa et al. Xerogel-Encapsulated W110A Secondary Alcohol Dehydrogenase from Thermoanaerobacter ethanolicus Performs Asymmetric Reduction of Hydrophobic Ketones in Organic Solvents (Angewandte Chemie (2007), vol. 46(17), pp. 3091-3094.*
Goldberg et al., Novel immobilization routes for the covalent binding of an alcohol dehydrogenase from Rhodococcus ruber DSM 44541., Tetrahedron: Asymmetry (2008), vol. 19, Issue 10, pp. 1171-1173.*
Hanefeld et al., Understanding enzyme immobilisation., Chem. Soc. Rev., (2009), vol. 38, pp. 453-468.*
Align Chemical (2010).*
chiralvision_product_list (last viewed on Jun. 13, 2017).*
Huisman et al. Practical chiral alcohol manufacture using ketoreductases., Curr Opin Chem Biol. (2010), vol. 14(2), pp. 122-129.*
Biocatalysis: Fundamentals and Applications; by Andreas S. Bommarius, Bettina R. Riebel-Bommarius (2004), p. 404.*
Babich et al., Chem. Eur. 18:6604-6609, 2012 (Year: 2012).*
Truppo et al., "Development of an Improved Immobilized CAL-B for the Enzymatic Resolution of a Key Intermediate to Odanacatib", Org. Process Res. Dev. 15:1033-1035, 2011.*
KRED Screening Kit, Apr. 29, 2013, 4 pages (Year: 2013).*
KRED FAQ, Apr. 29, 2013, 6 pages (Year: 2013).*
Brena, B. M. et al, Immobilization of Enzymes, Methods in Biotechnology: Immobilization of Enzymes and Cells, 2006, p. 15-30.
Devine, H. G. et al., Arthrobacter sp. KNK168 variant transaminase SEQ:110, Database Geneseq, 2011, p. 1-2.

(Continued)

*Primary Examiner* — David Steadman
(74) *Attorney, Agent, or Firm* — Janet E. Fair; Catherine D. Fitch

(57) ABSTRACT

The invention is directed to immobilized ketoreductases and methods of making and using them. Enzymes are protein molecules which serve to accelerate the chemical reactions of living cells (often by several orders of magnitude). Without enzymes, most biochemical reactions would be too slow to even carry out life processes. Enzymes display great specificity and are not permanently modified by their participation in reactions. Since they are not changed during the reactions, enzymes can be cost effectively used as catalysts for a desired chemical transformation.

1 Claim, No Drawings
Specification includes a Sequence Listing.

(56) References Cited

OTHER PUBLICATIONS

Hernandez, K. et al., Lipase B from Candida antarctica immobilized on octadecyl Sepabeads: A very stable biocatalyst in the presence of hydrogen peroxide, Process Biochemistry, 2011, p. 873-878, vol. 46.

Hilterhaus, L. et al, Practical application of different enzymes immobilized on sepabeads, Bioprocess Biosyst Eng, 2008, p. 163-171, vol. 31.

Internet, Immobead, Chiral Vision, 2009, p. 1-3-, 00.

Knezevic-Jugovic, Z. D. et al., The Immobilization of Lipase on Sepabeads: Coupling, Characterization and Application in Geranyl Butyrate Synthesis in a Low Aqueous System, Chemical Industry & Chemical Engineering Quarterly, 2008, p. 245-249, vol. 14, No. 4.

Martin, A. R. et al., Characterization of free and immobilized (S)-aminotransferase for acetophenone production, Appl Microbiol Biotechnol, 2007, p. 843-851, vol. 76.

Petkar, M. et al., Immobilization of lipases for non-aqueous synthesis, Journal of Molecurlar Catalysis B: Enzymatic, 2006, p. 83-90, vol. 39.

Savile, C. K. et al., Biocatalytic Asymmetric Synthesis of Chiral Amines from Ketones Applied to Sitagliptin Manufacture, Science, 2010, p. 305-, vol. 329.

Song-Se Yi, et al, Covalent immobilization of w-transaminase from Vibrio fluvialis JS17 on chitosan beads, Process Biochemistry, 2007, p. 895-898, 42.

Sun, J. et al., Immobilization of Candida antarctica lipase B by adsorption in organic medium, New Biotechnology, 2010, p. 53-, vol. 27, No. 1.

Truppo, M. D. et al, Development of an Immobilized Transaminase Capable of Operating in Organic Solvent, ChemCatChem, 2012, p. 1071-1074, vol. 4, No. 8.

Truppo, M. D. et al., Efficient kinetic resolution of racemic amines using a transaminase in combination with an amino acid oxidase, Chem. Commun, 2009, p. 2127-2129, 0.

Truppo, M. D. Eta L., Efficient Production of Enantiomerically Pure Chiral Amines at Concentrations of 50 g/L Using Transaminases, Organic Process Research & Development, 2010, p. 234-237, vol. 14.

Turner, N. J. et al., Chiral Amine Synthesis: Methods, Developments and Applications, Biocatalytic Routes to Nonracemic Chiral Amines, 2010, p. 441-455, 0.

Wang, P. et al., Asymmetric Biocatalytic reduction of 3,5-bis(trifluoromethyl) acetophenone to (1R)-[3,5-bis(trifluoromethyl)phenyl]ethanol using whole cells of newly isolated Leifsonia xyli HS0904, Appl Microbiol Biotechnol, 2011, p. 1897-1904, 90.

Huisman, Gjalt, W. et al., Practical chiral alcohol manufacture using ketoreductases, Current Opinion in Chemical Biology, 2010, p. 122-129, vol. 14.

Li, Hongmei, et al., Development of an Immobilized Ketoreductase for Enzymatic (R)-1-(3,5-Bis(trifluoromethyl) phenyl)ethanol Production, Organic Process Research & Development, 2015, p. 695-700, vol. 19.

Nagayama, Kazuhito, et al., Immobilization conditions of ketoreductase on enantioselective reduction in a gas-solid bioreactor, Biotechnology Journal, 2010, p. 520-525, vol. 5.

Petkova, Galina, A. et al., Synthesis of silica particles and their application as supports for alcohol dehydrogenases and cofactor immobilizations: Conformational changes that lead to switch in enzyme stereoselectivity, Biochimica et Biophysica Acta, 2012, p. 792-801, vol. 1824.

Shafiee, A. et al., Purification, characterization and immobilization of an NADPH-dependent enzyme involved in the chiral specific reduction of the keto ester M, Appl Microbial Biotechnol, 1998, p. 709-717, vol. 49.

* cited by examiner

IMMOBILIZED KETOREDUCTASES AND PROCESS FOR MAKING AND USING IMMOBILIZED KETOREDUCTASE

CROSS-REFERENCE TO RELATED APPLICATIONS

This application is a U.S. National Phase application under 35 U.S.C. § 371 of PCT Application No. PCT/US2014/023844, filed Mar. 12, 2014, which published as WO2014/150633A1 on Sep. 25, 2014, and claims priority under 35 U.S.C. § 365(b) from U.S. provisional patent application No. 61/898,503, filed Nov. 1, 2013 and U.S. provisional patent application No. 61/791,247, filed Mar. 15, 2013.

TECHNICAL FIELD OF THE INVENTION

The invention is directed to immobilized ketoreductases and methods of making and using them.

REFERENCE TO SEQUENCE LISTING, TABLE OR COMPUTER PROGRAM

The official copy of the Sequence Listing is submitted concurrently with the specification as an ASCII formatted text file via EFS-Web, with a file name "MRL-23079-US-PSP.txt", a creation date of Mar. 4, 2013, and a size of 2,610 bytes. The Sequence Listing filed via EFS-Web is part of the specification and is incorporated in its entirety by reference herein.

BACKGROUND OF THE INVENTION

Enzymes are protein molecules which serve to accelerate the chemical reactions of living cells (often by several orders of magnitude). Without enzymes, most biochemical reactions would be too slow to even carry out life processes. Enzymes display great specificity and are not permanently modified by their participation in reactions. Since they are not changed during the reactions, enzymes can be cost effectively used as catalysts for a desired chemical transformation.

Ketoreductases are a specific class of enzymes that catalyze the direct reduction of prochiral ketones to chiral alcohols. Enantiomerically pure chiral alcohols are key intermediates in a number of pharmaceutical compounds that possess a wide range of biological activities. Currently there is considerable effort underway to develop efficient catalytic methods for their preparation utilizing biocatalysts. Ketoreductases have emerged as promising biocatalysts for chiral alcohol production with approximately 30% of the reported industrial biotransformation using ketoreductases. Straathof, A. J.; Panke, S.; Schmid, A. Curr. Opin. Biotechnol. 2002, 13, 548-556.

For example, (–)-Bchlorodiisopinocampheylborane (i.e., (–)-DIP-Cl or (–)-Ipc$_2$BCl) was originally for the large scale manufacture of the allergy medication montelukast sodium (SINGULAIR). (–)-DIP-Cl was replaced with a ketoreductase which ultimately has lead to an enzymatic process that reduces waste, improves yield and safety, and eliminates the need for (–)-DIP-Cl. Liang, J.; Lalonde, J.; Borup, B.; et al. Org. Process Res. Dev. 2010, 14, 193-198.

Though advances in producing chiral alcohols using ketoreductases have been highly regarded, there still exits some drawbacks to the enzymatic process. Currently enzymatic processes can only be run in aqueous solvent systems, as the ketoreductases are not stable in 100% organic solvents or near 100% organic solvents. Additionally, during product alcohol isolation, the ketoreductase catalyst is deactivated and discarded resulting in the inability to reuse the catalyst.

Thus, though attempts have been made to immobilize ketoreductases none have been successful in overcoming their lack of stability, more specifically their lack of stability in organic solvents.

SUMMARY OF THE INVENTION

Described herein, immobilized ketoreductases comprising a ketoreductase are physically attached to a resin by ether adsorption or ionic bonds or covalent bonds. The immobilized ketoreductases described herein include ketoreductases that are capable of converting prochiral ketones to chiral alcohols in the presence of a cofactor to levels measurable by an analysis technique.

In certain embodiments, described herein are immobilized ketoreductases comprising a ketoreductase that is capable of converting prochiral ketones to chiral alcohols in the presence of a cofactor to levels measurable by an analysis technique; and a resin, wherein the recombinant ketoreductase is physically attached to the resin by adsorption or ionic bonds or covalent bonds, and wherein the immobilized ketoreductase is stable in a solvent system that comprises at least 90% of organic solvents.

For example in one embodiment, the ketoreductase is attached to a resin by adsorption. In another embodiment, the ketoreductase is attached to a resin by ionic bonds. In another embodiment, the ketoreductase is attached to a resin by covalent bonds.

The immobilized ketoreductases described herein are stable in organic solvents systems. As used herein stable immobilized ketoreductases mean that the immobilized ketoreductase retains its structural conformation or its activity, in organic solvent systems. In one embodiment described herein, the immobilized ketoreductase is stable in a solvent system that comprises at least 90% of organic solvents.

In certain embodiments described herein, the ketoreductase is a ketoreductase that is capable of converting prochiral ketones to chiral alcohols in the presence of a coenzyme to levels measurable by HPLC-UV absorbance.

In yet another embodiment the ketoreductase is selected from the group consisting of enzymes found in the CODEX KRED Panel purchased from CODEXIS in Redwood City, Calif. such as, but not limited to, P1B2, P1B10, P1D3, P1D5, P1H9, P1H10, P2B11, P2C2, P2D11, P3D1, P3D11, P3C3 and P3H2. ("P#" refers to the panel number and the following letter and number refer to the letter column and number row were the enzyme is located). In yet another embodiment the ketoreductase is selected from the group consisting of enzymes KRED 101, KRED 108, KRED 112, KRED 119, KRED 124, KRED 130, KRED 134, KRED NADH 101 and KRED NADH 102 purchased from BIO-CATALYTICS (now owned by CODEXIS). In still another embodiment the ketoreductase is SEQ ID NO. 1, or an active fragment thereof.

In certain embodiments of the immobilized ketoreductases described herein, the resin comprises polyacrylic with ester/alkyl functional groups, polymethacrylate with alkyl functional groups, polymethacrylate with ester/alkyl functional groups, polystyrene with aromatic functional groups, silica with hydroxyl functional groups, polyacrylic with epoxide functional groups, polymethacrylate with epoxide functional groups, polymethacrylate with amino epoxide functional groups, polyacrylic with carboxylic functional groups, polystyrene with quaternary ammonia functional groups, styrene/DVB copolymer or polymethacrylate with octadecyl functional groups. For example in one embodiment, the resin comprises styrene/DVB copolymer or polymethacrylate with octadecyl functional groups. In another example, the resin is polymethacrylate with epoxide functional groups or polymethacrylate with amino epoxide functional groups.

In other embodiments, the resin is selected from the group consisting of: LEWATIT VPOC 1600, SEPABEAD EXE120, DIAION HP2MG, IMMOBEAD-EC1, IMMOBEAD-S861, IMMOBEAD-S60S, IMMOBEAD-150A (APOLAR), IMMOBEAD-150P (POLAR), IMMOBEAD-350A (APOLAR), SEPABEAD EC-EP, SEPABEAD EC EP403, SEPABEAD EC EP703, SEPABEAD EXE 032, SEPABEAD EC-HFA/S, SEPABEAD EXE119, IMMOBEAD-D152, IMMOBEAD-C435, IMMOBEAD-A161, IMMOBEAD-A171 and IMMOBEAD-A369. For example in one embodiment, the resin is selected from the group consisting of: SEPABEADS EC-EP, SEPABEADS EC-HFA/S, IMMOBEAD-150A and DIAION HP2MG.

In one embodiment of the immobilized ketoreductase described herein, ketoreductase P1B2 is chemically attached to the resin IMMOBEAD-150A. In another embodiment of the immobilized ketoreductase described herein, ketoreductase P1B2 is chemically attached to the resin IMMOBEAD-150A via covalent bonds. In another embodiment, the ketoreductase P1B2's chemically attached to the resin SEPABEADS EC-HFA/S. In yet another embodiment, the ketoreductase P1B2's chemically attached to the resin SEPABEADS EC-HFA/S via covalent bonds.

In certain embodiments of the immobilized ketoreductases described herein, the resin comprises methacrylates. For example in one embodiment, the resin is synthesized from methacrylates, wherein the monomer and the crosslinker are methacrylates. In certain embodiments, the resin does not contain any aromatic compounds. In other embodiments, the resin is DIAION HP2MG (Mistubishi). DIAION HP2MG is a highly porous, methacrylate based adsorption resin which is synthesized only from methacrylates (monomer and crosslinker are methacrylates). DIAION HP2MG (Mistubishi) does not contain any aromatic compounds, and is considered an intermediate polarity adsorption resin. DIAION HP2MG (Mistubishi) is suitable for desalting and adsorption of organic compounds of relatively high polarity by using the more hydrophilic characteristics of the polymer matrix.

In one embodiment of the immobilized ketoreducatases described herein, ketoreductase KRED P1B2 is physically attached to the resin DIAION HP2MG (Mitsubishi). In another embodiment, the ketoreductase KRED P1B2 is physically attached to the resin DIAION HP2MG (Mitsubishi) via adsorbtion.

Also, described herein are methods of making and using the immobilized ketoreductases. The immobilized ketoreductases described herein can be used in batch reactions, wherein the immobilized ketoreductases can be filtered out after the reaction is complete and reused in other reactions. Alternatively, the immobilized ketoreductases described herein can be used in a continuous reaction system wherein the starting material is continuously passed over the immobilized ketoreductase and the product is collected.

Also described herein is a process of making an immobilized ketoreductase comprising:
1) incubating a solution of ketoreductase with a resin and an enzyme solution to form an immobilized ketoreductase;
2) filtering and rinsing the immobilized ketoreductase;
3) drying the immobilized ketoreductase.

DETAILED DESCRIPTION OF THE INVENTION

Definitions

"Adsorption" as used herein is the adhesion of atoms, ions, or molecules from a gas, liquid, or dissolved solid to a surface. Adsorption can include interactions such as hydrophobic or hydrophilic interations.

"Ketoreductase", also called "alcohol dehydrogenases (ADH)", is used herein to refer to a polypeptide having an enzymatic capability of reducing a ketone by transferring a hydride from a cofactor such as nicotinamide adenine dinucleotide (NADH) or nicotinamide adenine dinucleotide phosphate (NADPH).

"Protein", "polypeptide," and "peptide" are used interchangeably herein to denote a polymer of at least two amino acids covalently linked by an amide bond, regardless of length or post-translational modification (e.g., glycosylation, phosphorylation, lipidation, myristilation, ubiquitination, etc.). Included within this definition are D- and L-amino acids, and mixtures of D- and L-amino acids.

"Substrate" as used herein refers to hydride group acceptor, such as a ketone, that accepts the hydride group from a hydride group donor in a reaction mediated by a ketoreductase. Substrates can include a wide variety of ketone substrates which, upon accepting the hydride groups, are converted to chiral alcohol products.

"Cofactor" and "coenzyme" are used herein interchangeably to refer to an enzyme that in conjunction with a ketoreductase catalyzes the reduction of carbonyl groups or the oxidation of alcohols. A reaction starts with the binding of the cofactor to the enzyme. Next, the ketone substrate is bound to the enzyme. Substrate binding is followed by hydride transfer from the cofactor to the ketone to produce an alcohol. The enzyme then releases the product alcohol. The oxidized cofactor must now be transformed back into the reduced form to be used again. Suitable hydride group donors are nicotinamide adenine dinucleotide (NADH) or nicotinamide adenine dinucleotide phosphate (NADPH) cofactors.

"Chiral alcohol" refers to alcohols of general formula $R_1$—CH(OH)—$R_2$ wherein $R_1$ and $R_2$ are nonidentical and is employed herein in its broadest sense, including a wide variety of aliphatic and alicyclic compounds of different, and mixed, functional types, characterized by the presence of a primary alcohol group bound to a secondary carbon atom which, in addition to a hydrogen atom, carries either (i) a divalent group forming a chiral cyclic structure, or (ii) two substituents (other than hydrogen) differing from each other in structure or chirality. Divalent groups forming a chiral cyclic structure include, for example, 2-methylbutane-1,4-diyl, pentane-1,4-diyl, hexane-1,4-diyl, hexane-1,5-diyl, 2-methylpentane-1,5-diyl. The two different substituents on the secondary carbon atom ($R_1$ and $R_2$ above) also can vary widely and include alkyl, aryl, halo, hydroxy, lower alkyl, lower alkoxy, lower alkylthio, cycloalkyl, carboxy, carboalkoxy, carbamoyl, mono- and di-(lower alkyl) substituted carbamoyl, trifluoromethyl, phenyl, nitro, amino, mono- and di-(lower alkyl) substituted amino, alkylsulfonyl, arylsulfonyl, alkylcarboxamido, arylcarboxamido, etc., as well as alkyl, aralkyl, or aryl substituted by the foregoing.

"Nicotinamide adenine dinucleotide (NADH)" and "nicotinamide adenine dinucleotide phosphate (NADPH)" are used herein to refer to preferred cofactors in ketoreductase reactions.

"Naturally occurring" or "wild-type" refers to a form found in nature. For example, a naturally occurring or wild-type polypeptide or polynucleotide sequence is a sequence present in an organism that can be isolated from a source in nature and which has not been intentionally modified by human manipulation.

"Recombinant" when used with reference to, e.g., a cell, nucleic acid, or polypeptide, refers to a material, or a material corresponding to the natural or native form of the material, that has been modified in a manner that would not otherwise exist in nature, or is identical thereto but produced or derived from synthetic materials and/or by manipulation using recombinant techniques. Non-limiting examples include, among others, recombinant cells expressing genes that are not found within the native (non-recombinant) form of the cell or express native genes that are otherwise expressed at a different level.

"Percentage of sequence identity," "percent identity," and "percent identical" are used herein to refer to comparisons between polynucleotide sequences or polypeptide sequences, and are determined by comparing two optimally aligned sequences over a comparison window, wherein the portion of the polynucleotide or polypeptide sequence in the comparison window may comprise additions or deletions (i.e., gaps) as compared to the reference sequence for optimal alignment of the two sequences. The percentage is calculated by determining the number of positions at which either the identical nucleic acid base or amino acid residue occurs in both sequences or a nucleic acid base or amino acid residue is aligned with a gap to yield the number of matched positions, dividing the number of matched positions by the total number of positions in the window of comparison and multiplying the result by 100 to yield the percentage of sequence identity. Determination of optimal alignment and percent sequence identity is performed using the BLAST and BLAST 2.0 algorithms (see e.g., Altschul et al., 1990, J. Mol. Biol. 215: 403-410 and Altschul et al., 1977, Nucleic Acids Res. 3389-3402). Software for performing BLAST analyses is publicly available through the National Center for Biotechnology Information website.

Briefly, the BLAST analyses involve first identifying high scoring sequence pairs (HSPs) by identifying short words of length W in the query sequence, which either match or satisfy some positive-valued threshold score T when aligned with a word of the same length in a database sequence. T is referred to as, the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=-4, and a comparison of both strands. For amino acid sequences, the BLASTP program uses as defaults a wordlength (W) of 3, an expectation (E) of 10, and the BLOSUM62 scoring matrix (see Henikoff and Henikoff, 1989, Proc Natl Acad Sci USA 89:10915).

Numerous other algorithms are available that function similarly to BLAST in providing percent identity for two sequences. Optimal alignment of sequences for comparison can be conducted, e.g., by the local homology algorithm of Smith and Waterman, 1981, Adv. Appl. Math. 2:482, by the homology alignment algorithm of Needleman and Wunsch, 1970, J. Mol. Biol. 48:443, by the search for similarity method of Pearson and Lipman, 1988, Proc. Natl. Acad. Sci. USA 85:2444, by computerized implementations of these algorithms (GAP, BESTFIT, FASTA, and TFASTA in the GCG Wisconsin Software Package), or by visual inspection (see generally, Current Protocols in Molecular Biology, F. M. Ausubel et al., eds., Current Protocols, a joint venture between Greene Publishing Associates, Inc. and John Wiley & Sons, Inc., (1995 Supplement) (Ausubel)). Additionally, determination of sequence alignment and percent sequence identity can employ the BESTFIT or GAP programs in the GCG Wisconsin Software package (Accelrys, Madison Wis.), using default parameters provided.

"Substantial identity" refers to a polynucleotide or polypeptide sequence that has at least 80 percent sequence identity, preferably at least 85 percent sequence identity, more preferably at least 89 percent sequence identity, more preferably at least 95 percent sequence identity, and even more preferably at least 99 percent sequence identity as compared to a reference sequence over a comparison window of at least 20 residue positions, frequently over a window of at least 30-50 residues, wherein the percentage of sequence identity is calculated by comparing the reference sequence to a sequence that includes deletions or additions which total 20 percent or less of the reference sequence over the window of comparison. In specific embodiments applied to polypeptides, the term "substantial identity" means that two polypeptide sequences, when optimally aligned, such as by the programs GAP or BESTFIT using default gap weights, share at least 80 percent sequence identity, preferably at least 89 percent sequence identity, more preferably at least 95 percent sequence identity or more (e.g., 99 percent sequence identity). Preferably, residue positions which are not identical differ by conservative amino acid substitutions.

"Stereoselectivity" refers to the preferential formation in a chemical or enzymatic reaction of one stereoisomer over another. Stereoselectivity can be partial, where the formation of one stereoisomer is favored over the other, or it may be complete where only one stereoisomer is formed. When the stereoisomers are enantiomers, the stereoselectivity is referred to as enantioselectivity, the fraction (typically reported as a percentage) of one enantiomer in the sum of both. It is commonly alternatively reported in the art (typically as a percentage) as the enantiomeric excess (e.e.) calculated therefrom according to the formula [major enantiomer−minor enantiomer]/[major enantiomer+minor enantiomer]. Where the stereoisomers are diastereoisomers, the stereoselectivity is referred to as diastereoselectivity, the fraction (typically reported as a percentage) of one diastereomer in a mixture of two diastereomers, commonly alternatively reported as the diastereomeric excess (d.e.). Enantiomeric excess and diastereomeric excess are types of stereomeric excess.

"Highly stereoselective" refers to a chemical or enzymatic reaction that is capable of converting a substrate to its corresponding product with at least about 85% stereoisomeric excess.

"Conversion" refers to the enzymatic transformation of a substrate to the corresponding product. "Percent conversion" refers to the percent of the substrate that is converted to the product within a period of time under specified conditions. Thus, for example, the "enzymatic activity" or "activity" of a ketoreductase polypeptide can be expressed as "percent conversion" of the substrate to the product.

"Stable" refers to the ability of the immobilized enzymes described herein to retain their structural conformation and/or their activity in a solvent system that contains organic solvents. In certain embodiments, stable immobilized enzymes lose less than 10% activity per hour in a solvent system that contains organic solvents. Preferably, the stable immobilized enzymes described herein lose less than 9% activity per hour in a solvent system that contains organic solvents. Preferably, the stable immobilized enzymes described herein lose less than 8% activity per hour in a solvent system that contains organic solvents. Preferably, the stable immobilized enzymes described herein lose less than 7% activity per hour in a solvent system that contains organic solvents. Preferably, the stable immobilized enzymes described herein lose less than 6% activity per hour in a solvent system that contains organic solvents. Preferably, the stable immobilized enzymes described herein lose less than 5% activity per hour in a solvent system that contains organic solvents. Preferably, the stable immobilized enzymes described herein lose less than 4% activity per hour in a solvent system that contains organic solvents. Preferably, the stable immobilized enzymes described herein lose less than 3% activity per hour in a solvent system that contains organic solvents. Preferably, the stable immobilized enzymes described herein lose less than 2% activity per hour in a solvent system that contains organic solvents. Preferably, the stable immobilized enzymes described herein lose less than 1% activity per hour in a solvent system that contains organic solvents.

"Amino acid" or "residue" as used in context of the polypeptides disclosed herein refers to the specific monomer at a sequence position.

"Hydrophilic amino acid or residue" refers to an amino acid or residue having a side chain exhibiting a hydrophobicity of less than zero according to the normalized consensus hydrophobicity scale of Eisenberg et al., 1984, J. Mol. Biol. 179:125-142. Genetically encoded hydrophilic amino acids include L-Thr (T), L-Ser (S), L-His (H), L-Glu (E), L-Asn (N), L-Gln (Q), L-Asp (D), L-Lys (K) and L-Arg (R).

"Acidic amino acid or residue" refers to a hydrophilic amino acid or residue having a side chain exhibiting a pK value of less than about 6 when the amino acid is included in a peptide or polypeptide. Acidic amino acids typically have negatively charged side chains at physiological pH due to loss of a hydrogen ion. Genetically encoded acidic amino acids include L-Glu (E) and L-Asp (D).

"Basic amino acid or residue" refers to a hydrophilic amino acid or residue having a side chain exhibiting a pKa value of greater than about 6 when the amino acid is included in a peptide or polypeptide. Basic amino acids typically have positively charged side chains at physiological pH due to association with hydronium ion. Genetically encoded basic amino acids include L-Arg (R) and L-Lys (K).

"Polar amino acid or residue" refers to a hydrophilic amino acid or residue having a side chain that is uncharged at physiological pH, but which has at least one bond in which the pair of electrons shared in common by two atoms is held more closely by one of the atoms. Genetically encoded polar amino acids include L-Asn (N), L-Gln (Q), L-Ser (S) and L-Thr (T).

"Hydrophobic amino acid or residue" refers to an amino acid or residue having a side chain exhibiting a hydrophobicity of greater than zero according to the normalized consensus hydrophobicity scale of Eisenberg et al., 1984, J. Mol. Biol. 179:125-142. Genetically encoded hydrophobic amino acids include L-Pro (P), L-Ile (I), L-Phe (F), L-Val (V), L-Leu (L), L-Trp (W), L-Met (M), L-Ala (A) and L-Tyr (Y).

"Aromatic amino acid or residue" refers to a hydrophilic or hydrophobic amino acid or residue having a side chain that includes at least one aromatic or heteroaromatic ring. Genetically encoded aromatic amino acids include L-Phe (F), L-Tyr (Y), L-His (H) and L-Trp (W). L-His (H) histidine is classified herein as a hydrophilic residue or as a constrained residue.

"Non-polar amino acid or residue" refers to a hydrophobic amino acid or residue having a side chain that is uncharged at physiological pH and which has bonds in which the pair of electrons shared in common by two atoms is generally held equally by each of the two atoms (i.e., the side chain is not polar). Genetically encoded non-polar amino acids include L-Gly (G), L-Leu (L), L-Val (V), L-Ile (I), L-Met (M) and L-Ala (A).

"Aliphatic amino acid or residue" refers to a hydrophobic amino acid or residue having an aliphatic hydrocarbon side chain. Genetically encoded aliphatic amino acids include L-Ala (A), L-Val (V), L-Leu (L) and L-Ile (I).

"Cysteine" or L-Cys (C) is unusual in that it can form disulfide bridges with other L-Cys (C) amino acids or other sulfanyl- or sulfhydryl-containing amino acids. The "cysteine-like residues" include cysteine and other amino acids that contain sulfhydryl moieties that are available for formation of disulfide bridges. The ability of L-Cys (C) (and other amino acids with SH containing side chains) to exist in a peptide in either the reduced free SH or oxidized disulfide-bridged form affects whether L-Cys (C) contributes net hydrophobic or hydrophilic character to a peptide. While L-Cys (C) exhibits a hydrophobicity of 0.29 according to the normalized consensus scale of Eisenberg (Eisenberg et al., 1984, supra), it is to be understood that for purposes of the present disclosure L-Cys (C) is categorized into its own unique group.

"Hydroxyl-containing amino acid or residue" refers to an amino acid containing a hydroxyl (—OH) moiety. Genetically-encoded hydroxyl-containing amino acids include L-Ser (S) L-Thr (T) and L-Tyr (Y).

Ketoreductases

In general, ketoreductases catalyze the reduction of ketones to chiral alcohols. Examples of ketoreductases include any polypeptide having an enzymatic capability of transferring a hydride group from a cofactor to an acceptor carbonyl compound, converting the ketone into its corresponding alcohol:

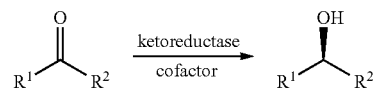

wherein each of $R^1$ and $R^2$ taken independently, is an alkyl, an alkylaryl group, or aryl group which is unsubstituted or substituted with one or more enzymatically non-inhibiting groups. $R^1$ and $R^2$ are different in structure. The groups $R^1$ and $R^2$, taken together, may form a ring that is unsubstituted, substituted, or fused to other rings.

Described herein are immobilized ketoreductases comprising recombinant ketoreductases that are capable of converting prochiral ketones to chiral alcohols in the presence of a cofactor to levels measurable by an analysis technique.

In certain embodiments of the immobilized ketoreductases described herein, the immobilized ketoreductases include ketoreductases that are capable of converting in the presence of a cofactor to levels measurable by an analysis technique, such as HPLC-UV absorbance.

In still yet other embodiments of the immobilized ketoreductases described herein, the immobilized ketoreductases include ketoreductases that are capable of improving conversion of prochiral ketones into chiral alcohols, as compared to using lyophilized enzymes in the presence of a cofactor to levels measurable by an analysis technique, such as HPLC-UV absorbance.

Suitable ketoreductases that can be used in the immobilized enzymes described herein, include naturally occurring or recombinant ketoreductases.

Examples of suitable ketoreductases that can be used in the immobilized enzymes described herein are selected from the group consisting of enzymes found in the CODEX KRED Panel purchased from CODEXIS in Redwood City, Calif. such as, but not limited to, P1B2, P1B10, P1D3, P1D5, P1H9, P1H10, P2B11, P2C2, P2D11, P3D1, P3D11, P3C3 and P3H2. In yet another embodiment the ketoreductase can be selected from the group consisting of enzymes KRED 101, KRED 108, KRED 112, KRED 119, KRED 124, KRED 130, KRED 134, KRED NADH 101 and KRED NADH 102 purchased from BIOCATALYTICS (now owned by CODEXIS). Such ketoreductases can be purchased from CODEXIS, Redwood City, Calif. In still another embodiment the ketoreductase is SEQ ID NO. 1, or an active fragment thereof.

Additional suitable ketoreductases are described in the following: U.S. Pat. No. 8,512,973; U.S. Pat. No. 8,470,572; U.S. Pat. No. 8,426,178; U.S. Pat. No. 8,415,127; U.S. Pat. No. 8,415,126; U.S. Pat. No. 8,288,141; U.S. Pat. No. 8,288,131; U.S. Pat. No. 8,273,554; U.S. Pat. No. 8,273,547; U.S. Pat. No. 8,257,952; U.S. Pat. No. 8,252,554; U.S. Pat. No. 8,227,229; U.S. Pat. No. 8,088,610; U.S. Pat. No. 8,071,347; U.S. Pat. No. 7,977,078; U.S. Pat. No. 7,883,879; U.S. Pat. No. 7,879,585; U.S. Pat. No. 7,833,767; U.S. Pat. No. 7,820,421; U.S. Pat. No. 7,816,111 and U.S. Pat. No. 7,629,157 which are incorporated herein in their entirety by reference.

In some embodiments, ketoreductases capable of converting the ketone substrate, in the presence of a cofactor to levels of product detectable by an analysis technique, such as HPLC-UV absorbance comprise an amino acid sequence corresponding to the sequence of SEQ ID NO. 1.

In some embodiments, the ketoreductases comprise an amino acid sequence that is at least about 80%, 85%, 86%, 87%, 88%, 89%, 90%, 91%, 92%, 93%, 94%, 95%, 96%, 97%, 98%, or 99% identical to SEQ ID NO. 1.

In other embodiments of the immobilized ketoreductases described herein, the ketoreductase is P1B2.

The immobilized ketoreductases described herein include a ketoreductase that is physically attached to a solid support by adsorption or chemically attached to a solid support by ionic or covalent bonds.

In certain embodiments of the immobilized ketoreductases described herein, the immobilized ketoreductases include a ketoreductase that is physically attached to a solid support by adsorption, specifically by hydrophobic interactions. Suitable ketoreductases include hydrophobic amino acids or residues i.e. amino acids or residues that include at least one side chain exhibiting a hydrophobicity of greater than zero according to the normalized consensus hydrophobicity scale of Eisenberg et al., 1984, J. Mol. Biol. 179:125-142. Genetically encoded hydrophobic amino acids include L-Pro (P), L-Ile (I), L-Phe (F), L-Val (V), L-Leu (L), L-Trp (W), L-Met (M), L-Ala (A) and L-Tyr (Y). In certain embodiments, the ketoreductases can include non-polar amino acids or residues such as, but not limited to L-Gly (G), L-Leu (L), L-Val (V), L-Ile (I), L-Met (M) and L-Ala (A). In other embodiments, the ketoreductases can include aliphatic amino acids or residues such as, but not limited to L-Ala (A), L-Val (V), L-Leu (L) and L-Ile (I). In still other embodiments, the ketoreductases can include aromatic amino acids or residues such as, but not limited to, L-Phe (F), L-Tyr (Y) and L-Trp (W).

In certain embodiments of the immobilized ketoreductases described herein, the ketoreductase is chemically attached to a solid support by covalent bonds. Suitable ketoreductases include acidic or basic amino acids or residues. Acidic amino acids include L-Glu (E) and L-Asp (D). Basic amino acids include L-Arg (R) and L-Lys (K). Other ketoreductases that can be chemically attached to a solid support include ketoreductases that include hydrophilic amino acids or residues, hydroxyl-containing amino acids or residues or polar amino acids or residues or ketoreductases. Still other ketoreductases that can be chemically attached to a solid support include ketoreductases that include cysteine. In one example, the ketoreductase contains L-Lys (K) which covalently bonds to a resin containing epoxide functionalities.

A suitable example of a ketoreductase that is chemically attached to a solid support, such as a resin, by covalent bonds is P1B2.

In certain embodiments of the immobilized ketoreductases described herein, the immobilized ketoreductases include a ketoreductase that is physically attached to a solid support through adsorption, specifically hydrophilic interactions. Suitable ketoreductases include acidic or basic amino acids or residues. Acidic amino acids include L-Glu (E) and L-Asp (D). Basic amino acids include L-Arg (R) and L-Lys (K). Other ketoreductases that can be physically attached to a solid support include ketoreductases that include hydrophilic amino acids or residues, hydroxyl-containing amino acids or residues or polar amino acids or residues or ketoreductases, such as Arg (R), Lys (K), His (H), Asn (N) and Pro (P). In certain embodiments, the ketoreductases can include non-polar amino acids or residues such as, but not limited to L-Gly (G), L-Leu (L), L-Val (V), L-Ile (I), L-Met (M) and L-Ala (A). In other embodiments, the ketoreductases can include aliphatic amino acids or residues such as, but not limited to L-Ala (A), L-Val (V), L-Leu (L) and L-Ile (I). In still other embodiments, the ketoreductases can include aromatic amino acids or residues such as, but not limited to, Arg (R), Lys (K), His (H), Asn (N) and Pro (P).

As described herein, the ketoreductase polypeptides of the disclosure can be in the form of fusion polypeptides in which the ketoreductase polypeptides are fused to other polypeptides, such as, by way of example and not limitation, antibody tags (e.g., myc epitope), purifications sequences (e.g., His tags for binding to metals), and cell localization signals (e.g., secretion signals). Thus, the ketoreductase polypeptides can be used with or without fusions to other polypeptides.

The polypeptides described herein are not restricted to the genetically encoded amino acids. In addition to the genetically encoded amino acids, the polypeptides described herein may be comprised, either in whole or in part, of naturally-occurring and/or synthetic non-encoded amino acids. Certain commonly encountered non-encoded amino acids of which the polypeptides described herein may be comprised include, but are not limited to: the D-stereoisomers of the genetically-encoded amino acids; 2,3-diaminopropionic acid (Dpr); α aminoisobutyric acid (Aib); ε aminohexanoic acid (Aha); δ aminovaleric acid (Ava); N-methylglycine or sarcosine (MeGly or Sar); ornithine (Orn); citrulline (Cit); t-butylalanine (Bua); t-butylglycine (Bug); N-methylisoleucine (MeIle); phenylglycine (Phg); cyclohexylalanine (Cha); norleucine (Nle); naphthylalanine (Nal); 2-chlorophenylalanine; 3-chlorophenylalanine; 4 chlorophenylalanine; 2 fluorophenylalanine; 3 fluorophenylalanine; 4 fluorophenylalanine (Pff); 2-bromophenylalanine (Obf); 3-bromophenylalanine (Mbf); 4-bromophenylalanine (Pbf); 2-methylphenylalanine (Omf); 3-methylphenylalanine (Mmf); 4-methylphenylalanine (Pmf); 2-nitrophenylalanine (Onf); 3-nitrophenylalanine (Mnf); 4-nitrophenylalanine (Pnf); 2-cyanophenylalanine; 3-cyanophenylalanine; 4-cyanophenylalanine; 2-trifluoromethylphenylalanine (Otf); 3-trifluoromethylphenylalanine (Mtf); 4-trifluoromethylphenylalanine (Ptf); 4-aminophenylalanine (Paf); 4-iodophenylalanine (Pif); 4-aminomethylphenylalanine (Pamf); 2,4-dichlorophenylalanine (Opef); 3,4-dichlorophenylalanine (Mpcf); 2,4-difluorophenylalanine (Opff); 3,4-difluorophenylalanine (Mpff); pyrid-2-yl-alanine (2pAla); pyrid-3-ylalanine (3pAla); pyrid-4-ylalanine (4pAla); naphth-1-ylalanine (1nAla); naphth-2-ylalanine (2nAla); thiazolylalanine (taAla); benzothienylalanine (bAla); thienylalanine (tAla); furylalanine (fAla); homophenylalanine (hPhe); homotyrosine (hTyr); homotryptophan (hTrp); pentafluorophenylalanine (5ff); styrylkalanine (sAla); authrylalanine (aAla); 3,3-diphenylalanine (Dfa); 3-amino-5-phenypentanoic acid (Afp); penicillamine (Pen); 1,2,3,4-tetrahydroisoquinoline-3-carboxylic acid (Tic); β 2-thienylalanine (Thi); methionine sulfoxide (Mso); N(w)-nitroarginine (nArg); homolysine (hLys); phosphonomethylphenylalanine (pmPhe); phosphoserine (pSer); phosphothreonine (pThr); homoaspartic acid (hAsp); homoglutamic acid (hGlu); 1-aminocyclopent-(2 or 3)-ene-4 carboxylic acid; pipecolic acid (PA), azetidine-3-carboxylic acid (ACA); 1-aminocyclopentane-3-carboxylic acid; allylglycine (aOly); propargylglycine (pgGly); homoalanine (hAla); norvaline (nVal); homoleucine (hLeu), homovaline (hVal); homoisoleucine (hIle); homoarginine (hArg); N acetyl lysine (AcLys); 2,4 diaminobutyric acid (Dbu); 2,3-diaminobutyric acid (Dab); N-methylvaline (MeVal); homocysteine (hCys); homoserine (hSer); hydroxyproline (Hyp) and homoproline (hPro). Additional non-encoded amino acids of which the polypeptides described herein may be comprised will be apparent to those of skill in the art (see, e.g., the various amino acids provided in Fasman, 1989, CRC Practical Handbook of Biochemistry and Molecular Biology, CRC Press, Boca Raton, Fla., at pp. 3-70 and the references cited therein, all of which are incorporated by reference). These amino acids may be in either the L or D configuration.

Those of skill in the art will recognize that the polypeptides described herein may comprise amino acids or residues bearing side chain protecting groups. Non-limiting examples of such protected amino acids, which in this case belong to the aromatic category, include (protecting groups listed in parentheses), but are not limited to: Arg(tos), Cys(methylbenzyl), Cys (nitropyridinesulfenyl), Glu(δ-benzylester), Gln(xanthyl), Asn(N-δ-xanthyl), His(bom), His(benzyl), His(tos), Lys(fmoc), Lys(tos), Ser(O-benzyl), Thr (O-benzyl) and Tyr(O-benzyl).

Non-encoding amino acids that are conformationally constrained of which the polypeptides described herein may be composed include, but are not limited to, N-methyl-amino acids (L-configuration); 1 aminocyclopent-(2 or 3)-ene-4-carboxylic acid; pipecolic acid; azetidine-3-carboxylic acid; homoproline (hPro); and 1 aminocyclopentane-3-carboxylic acid.

As described above the various modifications introduced into the naturally occurring polypeptide to generate an engineered ketoreductase enzyme can be targeted to a specific property of the enzyme.

In another aspect, the present disclosure provides polynucleotides encoding the improved ketoreductase polypeptides. The polynucleotides may be operatively linked to one or more heterologous regulatory sequences that control gene expression to create a recombinant polynucleotide capable of expressing the ketoreductase polypeptide. Expression constructs containing a heterologous polynucleotide encoding the engineered ketoreductase can be introduced into appropriate host cells to express the corresponding ketoreductase polypeptide.

Because of the knowledge of the codons corresponding to the various amino acids, availability of a protein sequence provides a description of all the polynucleotides capable of encoding the subject. The degeneracy of the genetic code, where the same amino acids are encoded by alternative or synonymous codons allows an extremely large number of nucleic acids to be made, all of which encode the improved ketoreductase polypeptides disclosed herein. Thus, having identified a particular amino acid sequence, those skilled in the art could make any number of different nucleic acids by simply modifying the sequence of one or more codons in a way which does not change the amino acid sequence of the protein. In this regard, the present disclosure specifically contemplates each and every possible variation of polynucleotides that could be made by selecting combinations based on the possible codon choices, and all such variations are to be considered specifically disclosed for any polypeptide disclosed herein.

In some embodiments, the polynucleotides can be selected and/or engineered to comprise codons that are preferably selected to fit the host cell in which the protein is being produced. For example, preferred codons used in bacteria are used to express the gene in bacteria; preferred codons used in yeast are used for expression in yeast; and preferred codons used in mammals are used for expression in mammalian cells. Since not all codons need to be replaced to optimize the codon usage of the ketoreductases (e.g., because the natural sequence can have preferred codons and because use of preferred codons may not be required for all amino acid residues), codon optimized polynucleotides encoding the ketoreductase polypeptides may contain preferred codons at about 40%, 50%, 60%, 70%, 80%, or greater than 90% of codon positions of the full length coding region.

Solid Support

Described herein are immobilized ketoreductases comprising a ketoreductase that is physically or chemically attached to a solid support. Support materials can comprise a wide range of material, either biological, nonbiological, organic, inorganic, or a combination of any of these. For example, the support material may be a polymerized Langmuir Blodgett film, functionalized glass, Si, Ge, GaAs, GaP, SiO$_2$, SiN$_4$, modified silicon, or any one of a wide variety of gels or polymers such as (poly)tetrafluoroethylene, (poly)vinylidenedifluoride, polystyrene, cross-linked polystyrene, polyacrylic, polylactic acid, polyglycolic acid, poly(lactide coglycolide), polyanhydrides, poly(methyl methacrylate), poly(ethylene-co-vinyl acetate), polysiloxanes, polymeric silica, latexes, dextran polymers, epoxies, polycarbonate, or combinations thereof. Support materials can be planar crystalline support materials such as silica based support materials (e.g. glass, quartz, or the like), or crystalline support materials used in, e.g., the semiconductor and microprocessor industries, such as silicon, gallium arsenide and the like. Silica aerogels can also be used as support materials, and can be prepared by methods known in the art. Aerogel support materials may be used as free standing substrates or as a surface coating for another support material.

A support material can take any form or shape and typically is a plate, slide, bead, pellet, disk, particle, strand, precipitate, membrane, optionally porous gel, sheets, tube, sphere, container, capillary, pad, slice, film, chip, multiwell plate or dish, optical fiber, etc. Although typically the support material takes an inanimate form, for some attachment peptide applications such as flow cytometry or in situ hybridization, it can be any form that is rigid or semi-rigid. The support material may contain raised or depressed regions on which a capture probe is located. The surface of the support material can be etched using well known techniques to provide for desired surface features, for example trenches, v-grooves, mesa structures, or the like.

Surfaces on the support material can be composed of the same material as the interior part of the support or can be made from a different material, and can be coupled to the interior support material by chemical or physical means. Such coupled surfaces may be composed of any of a wide variety of materials, for example, polymers, plastics, resins, polysaccharides, silica or silica-based materials, carbon, metals, inorganic glasses, membranes, or any of the above-listed support materials. In one embodiment, the surface is optically transparent and can have surface Si—OH functionalities, such as those found on silica surfaces.

Glass or plastic microscope slides have commonly been used as solid matrix supports for microarray analysis. Opaque matrix-coating materials used to produce microarrays include nylon, PVDF (polyvinylidene fluoride) and nitrocellulose. Nitrocellulose, a traditional polymer substrate in use for more than 50 years, can be used for microarray attachment applications. (E.g., Tonkinson and Stillman, Frontiers in Bioscience 7:c1-12, 2002.). Opaque nitrocellulose has been extensively used to immobilize proteins and nucleic acids for biomolecular analysis. Nitrocellulose immobilizes molecules of interest in near quantitative fashion and allows for short and long term storage. Nitrocellulose also allows for solution phase target species to efficiently bind to immobilized entities.

A solid support may be of any suitable composition to which the attachment molecule may be applied. It may be pretreated or functionalized prior to application of the attachment/molecule peptide to facilitate binding of the attachment molecules, or for any other desired purpose, such as fostering conditions favorable for the activity or any other desired property of the entity or avoiding undesired interactions with other entities. Many such surface treatments and/or functionalizations are known in the art and selection of a suitable treatment and/or functionalization will depend upon the identity and characteristics of the attachment molecule/peptide and entity and upon the attendant conditions and desired activity.

With regard to the immobilized ketoreductases described herein the solid support is a resin. Resins can be made from any suitable composition including, but not limited to, polyacrylate, polymethacrylate, polysrene, silica, and styrene/DVB copolymer. Such resins can include functional groups and facilitate adsorption, convalent bonding or ionic bonding of the ketoreductase to the resin. Suitable functional groups include, but are not limited to, epoxide, ester, alkyl aromatic groups, hydroxyl, carboxylic groups, quaternary ammonia and amino epoxide. Additionally, other functional groups such as octadecyl and resins that include a porous structure facilitate adsorption of the ketoreductase.

In certain embodiments of the immobilized ketoreductases described herein, the resin comprises polyacrylic with ester/alkyl functional groups, polymethacrylate with alkyl functional groups, polymethacrylate with ester/alkyl functional groups, polystyrene with aromatic functional groups, silica with hydroxyl functional groups, polyacrylic with epoxide functional groups, polymethacrylate with epoxide functional groups, polymethacrylate with amino epoxide functional groups, polyacrylic with carboxylic functional groups polystyrene with quatenary ammonia (quat. amm.) functional groups, styrene/DVB copolymer or polymethacrylate with octadecyl functional groups. For example in one embodiment, the resin comprises styrene/DVB copolymer or polymethacrylate with octadecyl functional groups. In another example, the resin is polymethacrylate with epoxide functional groups or polymethacrylate with amino epoxide functional groups.

Examples of suitable resins include, but are not limited to, LEWATIT VPOC 1600, SEPABEAD EXE120, DIAION HP2MG, IMMOBEAD-EC1, IMMOBEAD-S861, IMMOBEAD-S60S, IMMOBEAD-150A (APOLAR), IMMOBEAD-150P (POLAR), IMMOBEAD-350A (APOLAR), SEPABEAD EC-EP, SEPABEAD EC EP403, SEPABEAD EC EP703, SEPABEAD EXE 032, SEPABEAD EC-HFA/S, SEPABEAD EXE119, IMMOBEAD-D152, IMMOBEAD-C435, IMMOBEAD-A161, IMMOBEAD-A171 and IMMOBEAD-A369.

The following table includes suitable resins that can be used in connection with the immobilized ketoreductases described herein:

TABLE 1

| Resin name | Resin Composition | Resin Functional Group | Binding |
| --- | --- | --- | --- |
| Lewatit VPOC 1600 | polyacrylic | ester/alkyl | adsorption |
| SepaBead EXE120 | polymethacrylate | alkyl | adsorption |
| Diaion HP2MG | polymethacrylate | ester/alkyl | adsorption |
| Immobead-EC1 | polyacrylic | ester/alkyl | adsorption |
| Immobead-S861 | polystyrene | aromatic | adsorption |
| Immobead-S60S | silica | hydroxyl | adsorption |
| Immobead-150A (apolar) | polyacrylic | epoxide | covalent |
| Immobead-150P (polar) | polyacrylic | epoxide | covalent |
| Immobead-350A (apolar) | polyacrylic | epoxide | covalent |
| SepaBead EC-EP | polymethacrylate | epoxide | covalent |
| SepaBead EC EP403 | polymethacrylate | epoxide | covalent |
| SepaBead EC EP703 | polymethacrylate | epoxide | covalent |
| SepaBead EXE 032 | polymethacrylate | epoxide | covalent |
| SepaBead EC-HFA/S | polymethacrylate | amino epoxide | covalent |
| SepaBead EXE119 | polymethacrylate | epoxide | covalent |
| Immobead-D152 | polyacrylic | carboxylic | cationic |
| Immobead-C435 | polyacrylic | carboxylic | cationic |
| Immobead-A161 | polystyrene | quat. Amm | anionic |
| Immobead-A171 | polystyrene | quat. Amm | anionic |
| Immobead-A369 | polystyrene | quat. Amm | anionic |

In certain embodiments of the immobilized described herein, the immobilized ketoreductase includes a resin that is physically attached to the ketoreductase via adsorption. Suitable resins comprise styrene/DVB copolymer, polymethacrylate with octadecyl functional groups, polyacrylic with ester/alkyl functional groups, polymethacrylate with alkyl or ester/alkyl functional groups, polystyrene with aromatic functional groups or silica with hydroxyl functional groups. Examples include, but are not limited to, SEPABEADS EXA252, LEWATIT VPOC 1600, SEPABEAD EXE120, DIAION HP2MG, IMMOBEAD-EC1, IMMOBEAD-5861, IMMOBEAD-S60S and SEPABEADS EXE120.

In other embodiments of the immobilized ketoreductases described herein, the immobilized ketoreductase includes a resin that is chemically attached to a ketoreductase by covalent bonds. Suitable resins comprise polymethacrylate with epoxide functional groups, polyacrylic with epoxide functional groups or polymethacrylate with amino epoxide functional groups. Examples include, but are not limited to, IMMOBEAD-150A (APOLAR), IMMOBEAD-150P (POLAR), IMMOBEAD-350A (APOLAR), SEPABEAD EC-EP, SEPABEAD EC EP403, SEPABEAD EC EP703, SEPABEAD EXE 032, SEPABEAD EC-HFA/S and SEPABEAD EXE119.

In other embodiments of the immobilized ketoreductases described herein, the immobilized ketoreductase includes a resin that is chemically attached to a ketoreductase by ionic bonds. Suitable resins comprise polyacrylic with carboxylic or quatenary ammonia functional groups. Examples include, but are not limited to, IMMOBEAD-D152, IMMOBEAD-C435, IMMOBEAD-A161, IMMOBEAD-A171 and IMMOBEAD-A369.

In still other embodiments of the immobilized ketoreductases described herein, the immobilized ketoreductase is comprised of the ketoreductase P1B2 chemically attached to the resin SEPABEADS EXEEC-HFA/S (Mitsubishi). In still other embodiments of the immobilized described herein, the immobilized ketoreductase is comprised of the ketoreductase P1B2 chemically attached to the resin IMMOBEAD-150A (APOLAR) (Mitsubishi).

In certain embodiments of the immobilized ketoreductases described herein, the immobilized ketoreductase includes a resin that is physically attached to the ketoreductase. Suitable resins comprise methacrylates with no aromatic compounds or other functional groups. Examples include, but are not limited to, DIAION HP2MG (Mitsubishi).

In still other embodiments of the immobilized described herein, the immobilized ketoreductase is comprised of the ketoreductase P1B2 physically attached to the resin DIAION HP2MG (Mitsubishi).

Process for Making the Immobilized Ketoreductase

Also described herein are processes for making the immobilized ketoreductase. In certain embodiments of the processes for making the immobilized ketoreductases described herein, the process begins with making a buffered solution of the ketoreductase.

In some embodiments of the processes for making the immobilized ketoreductase, the ketoreductase solution can comprise a pH of about 5.0 to about 9.0. In some embodiments, the reaction condition for the process is a pH of about 7.0.

The process further comprises contacting or incubating the ketoreductase with a resin, by adding the resin to the solution. The solution is then agitated for a length of time, such as overnight.

In some embodiments, the reaction condition for carrying out the process can comprise a temperature of about 5° C. to about 70° C. In some embodiments, the reaction condition is a temperature of about 25° C. (room temperature).

Once the reaction is complete, the immobilized ketoreductase is filtered and rinsed. After the immobilized enzyme is rinsed with buffer, in certain embodiments of the processes described herein, the preparation is dried before it is used in a 90% organic solvent system. The immobilized enzyme can be dried under vacuum with a nitrogen sweep to remove water from the outer surface of the immobilized enzyme resin. The immobilized preparation can be stirred while drying to allow for even moisture content throughout the immobilized enzyme bed and to prevent over- or under-drying any portion of the immobilized enzyme preparation. Over-drying can result in loss of activity as water is stripped away from the enzyme molecule attached to the resin. Under-drying can result in insufficient mass transfer in an organic solvent system to affect the reduction of the desired substrate.

Processes for Using the Immobilized Ketoreductase

The immobilized ketoreductases described herein can be used to transfer a hydride from a cofactor such as nicotinamide adenine dinucleotide (NADH) or nicotinamide adenine dinucleotide phosphate (NADPH). Such a process comprises binding of the cofactor to the enzyme. Next, the ketone substrate is bound to the enzyme. Substrate binding is followed by hydride transfer from the cofactor to the ketone to produce an alcohol. The enzyme then releases the product alcohol and the oxidized cofactor is transformed back into the reduced from to be used again.

In some embodiments of the processes above, the compound of formula (I), the compound of formula (Ia) or the compound of formula (II) or compound of formula (III) is produced in at least 70%, 80%, 90%, 91%, 92%, 93%, 94%, 95%, 96%, 97%, 98%, 99% or more enantiomeric excess.

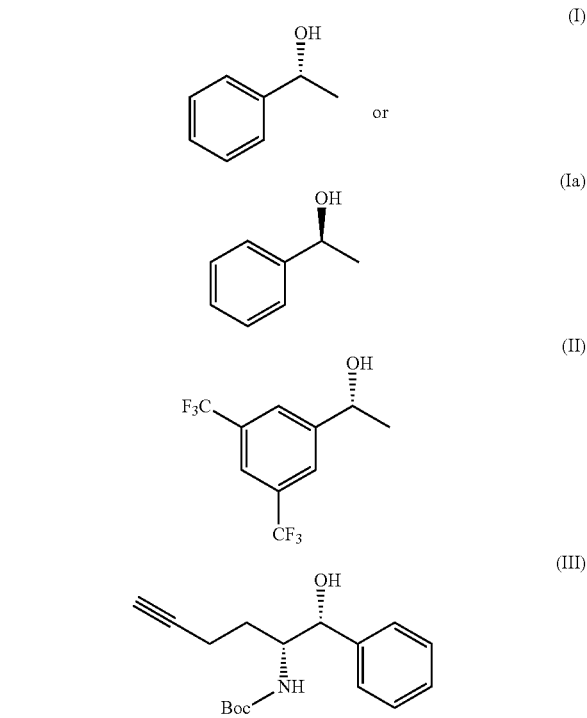

In some embodiments of the processes, the compound of formula (I), the compound of formula (Ia) or the compound of formula (II) or compound of formula (III) is produced in at least 99% enantiomeric excess.

In some embodiments, the process of using the immobilized ketoreductases described herein comprises the step of: dissolving an immobilized ketoreductase described herein in the presence of a cofactor.

Described herein are immobilized ketoreductases comprising a recombinant ketoreductase which is physically or chemically attached to a resin by covalent bonds, hydrophilic interactions or hydrophobic interactions, wherein the ketoreductase is stable in organic solvents. Suitable organic solvents that can be used in the processes described herein include any organic solvent commonly known in the art such as, toluene, methyl tert-butyl ether, methyltetrahydrofuran (Me-THF), cyclopentyl methyl ether (CPME), dichloromethane (DCM) methanol, ethanol, tetrahydrofuran (THF), dimethyl sulfoxide (DMSO), isopropylacetate, hexanes, propanol, isopropyl alcohol, bezene, acetone, xylene, methylethyl ketone, ether and ethyl acetate. In certain examples of the processes described herein the organic solvent is isopropyl alcohol.

In certain embodiments the organic solvent is a non-water saturated solvent. In other embodiments the organic solvent is a water-saturated solvent. Water saturation may keep the immobilized enzyme at a constant water concentration and prevent further drying of the immobilized enzyme over the course of the reaction. This can allow for greater operational stability when the immobilized enzyme is isolated at the end of the reaction and reused for multiple batches. In certain examples of the processes described herein the organic solvent is water-saturated isopropanol.

In certain embodiments the solvent that the ketoreductase is stable in is a component of a solvent system. In certain embodiments of the processes for using the immobilized ketoreductases described herein, the solvent system is a 100% organic solvent system. In other embodiments the solvent system contains 50-60% organic solvents. Preferably, the solvent system contains 60-70% organic solvents. More preferably, the solvent system contains 70-80% organic solvents. More preferably, the solvent system contains 80-90% organic solvents. More preferably, the solvent system contains 90-100% organic solvents. In other embodiments the solvent system contains at least 50% organic solvents. In other embodiments the solvent system contains at least 55% organic solvents. Preferably, the solvent system contains at least 60% organic solvents. Preferably, the solvent system contains at least 65% organic solvents. More preferably, the solvent system contains at least 70% organic solvents. More preferably, the solvent system contains at least 75% organic solvents. More preferably, the solvent system contains at least 80% organic solvents. More preferably, the solvent system contains at least 85% organic solvents. More preferably, the solvent system contains at least 90% organic solvents. More preferably, the solvent system contains at least 95% organic solvents. More preferably, the solvent system contains at least 100% organic solvents. The solvent system can contain more than one organic solvent, wherein the immobilized ketoreductase is stable in one or all of the organic solvents present in the solvent system.

As discussed above, ketoreductases catalyze the reduction of ketones to chiral alcohols by transferring a hydride group from a cofactor to an acceptor carbonyl compound, converting the ketone into its corresponding alcohol. Suitable cofactors include but are not limited to, nicotinamide adenine dinucleotide (NADH) or nicotinamide adenine dinucleotide phosphate (NADPH) cofactors.

In certain examples of the processes described herein the immobilized ketoreductase is the ketoreductase P1B2 physically attached to the resin DIANION HP2MG (Mitsubishi). In certain examples of the processes described herein the immobilized ketoreductase is the ketoreductase SEQ ID NO: 1 physically attached to the resin (Mitsubishi). In some embodiments of the processes described above, the immobilized ketoreductases described herein can be recycled, wherein once the immobilized ketoreductases are filtered off once the reaction is complete and used in subsequent reactions. Thus certain processes described herein can further comprise the step of filtering off the immobilized ketoreductase and to be used in subsequent reactions.

The processes of using the immobilized ketoreductases described herein include batch process and continuous process. Continuous processes include processes wherein the ketone substrate is continuously contacting the immobilized ketoreductase and wherein the product is continuously being collected. Examples include wherein the immobilized ketoreductase is packed in a column and a solution of the ketone substrate is passed through the column. Thus the ketone is continuously contacting the immobilized resin and the product is collected after is has passed through the column.

In some embodiments, the process for converting ketone substrate comprises dissolving the substrate in isopropyl alcohol; contacting the substrate with an immobilized ketoreductase described herein under reaction conditions of a temperature of 30 to 70° C., wherein at least 80%, 85%, 90%, 92%, 94%, 96%, or 98% or more of the ketone substrate is converted to product in 24 hrs. In some embodiments, the immobilized ketoreductase capable of carrying out the foregoing reaction comprises an amino acid sequence corresponding to P1B2, P1B10, P1D3, P1D5, P1H9, P1H10, P2B11, P2C2, P2D11, P3D1, P3D11, P3C3, P3H2, KRED 101, KRED 108, KRED 112, KRED 119, KRED 124, KRED 130, KRED 134, KRED NADH 101 or KRED NADH 102 and is physically or chemically attached to a resin comprising LEWATIT VPOC 1600, SEPABEAD EXE120, DIAION HP2MG, IMMOBEAD-EC1, IMMOBEAD-S861, IMMOBEAD-S60S, IMMOBEAD-150A (APOLAR), IMMOBEAD-150P (POLAR), IMMOBEAD-350A (APOLAR), SEPABEAD EC-EP, SEPABEAD EC EP403, SEPABEAD EC EP703, SEPABEAD EXE 032, SEPABEAD EC-HFA/S, SEPABEAD EXE119, IMMOBEAD-D152, IMMOBEAD-C435, IMMOBEAD-A161, IMMOBEAD-A171 or IMMOBEAD-A369.

In some embodiments, the processes above can further comprise the step of isolating the compound of structural formula (I), the compound of structural formula (II), the compound of structural formula (III), or the compound of structural formula (1a) from the reaction solvent.

EXAMPLES

General Scheme: Immobilization of Ketoreductase Enzyme

Ketoreductase enzyme and cofactor is added to a solution of sodium potassium phosphate in water at ambient temperature and is dissolved with gentle agitation. Resin is added. The mixture is gently agitated at 25° C. for at least 16 hours or settled in the refrigerator (4° C.) for at least 3 days. The resin is drained of all solution. The wet resin is washed with a solution of potassium dibasic phosphate and subsequently drained.

Ketone Reduction Procedure:

Immobilized Ketoreductase enzyme was added to a solution of ketone dissolved in organic solvent mixture with or without cofactor. The mixture was agitated at 30° C. for about 24 hours. The batch was filtered and concentrated.

Examples 1-20: Immobilization of Ketoreductase with Different Resins

Twenty different resins, as shown in Table 2, were evaluated.

TABLE 2

| Example | Resin name | Resin Composition | Resin Functional Group | Binding |
|---|---|---|---|---|
| 1 | Lewatit VPOC 1600 | polyacrylic | ester/alkyl | adsorption |
| 2 | SepaBeadEXE120 | polymethacrylate | alkyl | adsorption |
| 3 | Diaion HP2MG | polymethacrylate | ester/alkyl | adsorption |
| 4 | Immobead-EC1 | polyacrylic | ester/alkyl | adsorption |
| 5 | Immobead-S861 | polystyrene | aromatic | adsorption |
| 6 | Immobead-S60S | silica | hydroxyl | adsorption |
| 7 | Immobead-150A (apolar) | polyacrylic | epoxide | covalent |
| 8 | Immobead-150P (polar) | polyacrylic | epoxide | covalent |
| 9 | Immobead-350A (apolar) | polyacrylic | epoxide | covalent |
| 10 | SepaBead EC-EP | polymethacrylate | epoxide | covalent |
| 11 | SepaBead EC EP403 | polymethacrylate | epoxide | covalent |
| 12 | SepaBead EC EP703 | polymethacrylate | epoxide | covalent |
| 13 | SepaBead EXE 032 | polymethacrylate | epoxide | covalent |
| 14 | SepaBead EC-HFA/S | polymethacrylate | amino epoxide | covalent |
| 15 | SepaBead EXE119 | polymethacrylate | epoxide | covalent |
| 16 | Immobead-D152 | polyacrylic | carboxylic | cationic |
| 17 | Immobead-C435 | polyacrylic | carboxylic | cationic |
| 18 | Immobead-A161 | polystyrene | quat. Amm | anionic |
| 19 | Immobead-A171 | polystyrene | quat. Amm | anionic |
| 20 | Immobead-A3 69 | polystyrene | quat. Amm | anionic |

20 mg P1B2 (Ketoreductase from CODEXIS) with or without 2 mg NADP was dissolved in 2 ml 100 mM potassium phosphate buffer (pH 7). 100 mg of wet resin was added and the mixture was incubated for about 24 hours. The resin was then filtered and rinsed with 100 mM potassium phosphate buffer (pH 6.5-7) with or without 2 g/L NADP and dried.

Resin performance was evaluated versus the lyophilized ketoreductase in the following ketoreducation:

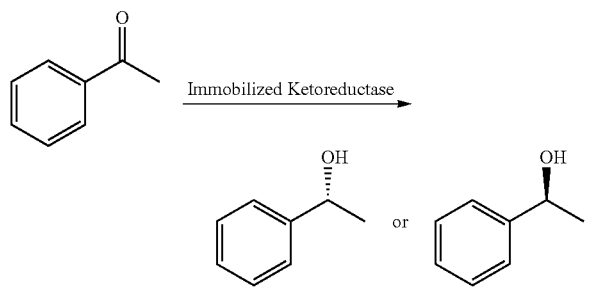

Reaction Procedure with Lyophilized Ketoreductase:

5 mg lyophilized ketoreductase and 1 mg cofactor NADP were gently dissolved in 0.9 ml 100 mM potassium phosphate buffer (pH 7), followed by addition of 10 mg acetophenone substrate in 0.1 ml 2-propanol. The reaction was aged at 30° C. for 16 hrs.

Reaction Procedure with Immobilized Ketoreductase:

100 mg immobilized ketoreductase and 0.1 mg cofactor NADP and 10 mg acetophenone substrate were added in 0.9 ml 2-propanol and 0.1 ml water. The reaction was aged at 30° C. for 16 hrs.

The immobilized ketoreductase preparations were active and reusable in 90% isopropyl alcohol and 10% water.

Examples 21-43: Immobilization of Different Ketoreductase

Twenty three different ketoreductase enzymes, as shown in Table 3, were evaluated.

TABLE 3

| Example | Ketoreductase from Codexis | CODEX KRED Screening Kit |
|---|---|---|
| 21 | P1B2 | Plate 1, Column B, Row 2 |
| 22 | P1B10 | Plate 1, Column B, Row 10 |
| 23 | P1D3 | Plate 1, Column D, Row 3 |
| 24 | P1D5 | Plate 1, Column D, Row 5 |
| 25 | P1H9 | Plate 1, Column H, Row 9 |
| 26 | P1H10 | Plate 1, Column H, Row 10 |
| 27 | P2B11 | Plate 2, Column B, Row 11 |
| 28 | P2C2 | Plate 2, Column C, Row 2 |
| 29 | P2D11 | Plate 2, Column D, Row 11 |
| 30 | P3D1 | Plate 3, Column D, Row 1 |
| 31 | P3D11 | Plate 3, Column D, Row 11 |
| 32 | P3C3 | Plate 3, Column C, Row 3 |
| 33 | P3H2 | Plate 1, Column B, Row 2 |
| 34 | KRED 101 | BIOCATALISIS, now owned by Codexis |
| 35 | KRED 108 | BIOCATALISIS, now owned by Codexis |
| 36 | KRED 112 | BIOCATALISIS, now owned by Codexis |
| 37 | KRED 119 | BIOCATALISIS, now owned by Codexis |
| 38 | KRED 124 | BIOCATALISIS, now owned by Codexis |
| 39 | KRED 130 | BIOCATALISIS, now owned by Codexis |
| 40 | KRED 134 | BIOCATALISIS, now owned by Codexis |
| 41 | KRED NADH 101 | BIOCATALISIS, now owned by Codexis |
| 42 | KRED NADH 102 | BIOCATALISIS, now owned by Codexis |
| 43 | KRED 208 | SEQ ID NO: 1 |

20 mg enzyme with or without 2 mg NADP or NAD was dissolved in 2 ml 100 mM potassium phosphate buffer (pH 7). 100 mg wet resin (Immobead-150A, Immobead-150P or SepaBead EC-HFA/S) was added the mixture was and incubated for about 24 hours. The solution was decanted and rinsed with 100 mM potassium phosphate buffer (pH 6.5-7) and dried.

Resin performance was evaluated versus the lyophilized ketoreductase in the following ketoreduction:

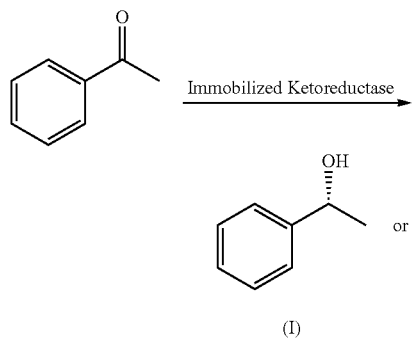

Reaction Procedure with Lyophilized Ketoreductase:

5 mg lyophilized ketoreductase and 1 mg cofactor NADP or NAD were gently dissolved in 0.9 ml 100 mM potassium phosphate buffer (pH 7 followed by addition of 10 mg acetophenone substrate in 0.1 ml 2-propanol and aging the reaction at 30° C. for 16 hrs.

Reaction Procedure with Immobilized Ketoreductase:

100 mg immobilized ketoreductase and 0.1 mg cofactor NADP and 10 mg acetophenone substrate were added in 0.9 ml 2-propanol and 0.1 ml water and the reaction was aged at 30° C. for 16 hrs. Using immobilized P1H10 gave R-alcohol product and immobilized P3C3 and P3H2 gave S-alcohol product respectively.

The immobilized ketoreductase preparations were active and reusable in 90% isopropyl alcohol and 10% water.

Example 44

Immobilized ketoreductases were also tested with 2,2,2,4'-tetrafluoroacetophenone substrate.

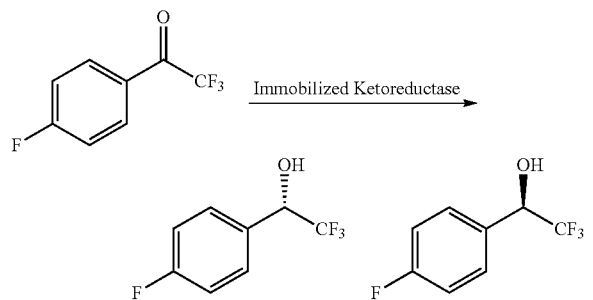

100 mg immobilized ketoreductase and 20 mg 2,2,2,4'-tetrafluroacetophenone substrate were added to a mixture/solution of 0.9 ml 2-propanol and 0.1 ml water and the reaction was aged at 30° C. for 16 hrs. Using immobilized P1B2 gave R-alcohol product and immobilized KRED NADH 102 gave S-alcohol product respectively.

Example 46

1-(3,5-bis(trifluoromethyl)phenyl)ethanone was examined with immobilized ketoreductase to form chiral alcohols which is one of the key intermediates of synthesis of EMEND (aprepitant). (reference: JACS, 125, 2129-2135, 2003; Tetrahedron: Asymmetry 17 (2006) 554-559)

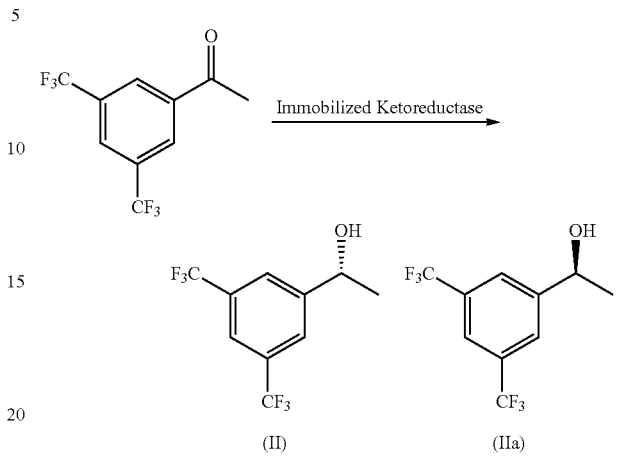

Immobilization Procedure of Ketoreductase P1B2

To 20 ml 0.1M buffer solution of sodium potassium phosphate at pH 7.0 was added P1B2 (2 g) and dissolved with gentle agitation. Resin IB-150A (10 g) or SepaBead EC-HFA/S (10 g) was added and the mixture was aged at 25° C. for 24-48 hours. The resin was filtered and washed with 0.1M solution of sodium potassium phosphate and dried. Resin was stored at 4° C.

Ketone Reduction Procedure with Immobilized Ketoreductase 100 mg immobilized P1B2 and 50 mg 1-(3,5-bis(trifluoromethyl)phenyl)ethanone were added to 0.9 ml 2-propanol and 0.1 ml water, aged at 30° C. for 16 hrs. The reaction reached full conversion and gave R-alcohol product with >99% ee. This product is one of the key intermediates to synthesis of aprepitant. Similarly using immobilized KRED 101 can obtain S-alcohol product.

Example 47

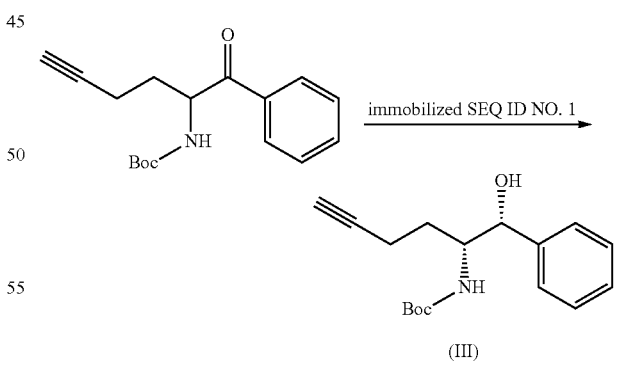

Immobilization of SEQ ID NO. 1

To 20 ml 0.1M buffer solution of sodium potassium phosphate at pH 7.0 was charged SEQ ID NO. 1 (2 g) and dissolved with gentle agitation. Resin IB-150A (10 g) was added and the mixture was aged at 25° C. for 24-48 hours. The resin was filtered and washed with 0.1M solution of sodium potassium phosphate and dried. Resin was stored at 4° C.

Ketone Reduction Procedure with Immobilized SEQ ID NO. 1

To a 250 ml flask was added 90 ml IPA and 10 ml water, ketone A (5 g, 17.4 mmol) and 1,4-diazabicyclooctane (9.76 g, 87.0 mmol, 5 eq) at 25° C. Immobilized SEQ ID NO. 1 (2.5 g, 50 wt %) was added and the reaction was heated to 50° C. with gentle agitation and aged for about 28 hours. Typically, the reaction gave 98% conversion, 99% ee and 100:1 Dr. The reaction was cooled to 25° C. and filtered to remove immobilized SEQ ID NO. 1. The recovered immobilized SEQ ID NO. 1 can be charged to fresh solution of ketone/DABCO IPA/water solution, and recycled up to 9 rounds while reaching specifications for conversion and selectivity. After removing immobilized enzyme, the crude reaction solution was azeotropically dried to remove water and reduce reaction volume to ~5 volumes IPA, then charged Phosphoric acid (5 eq, 1:1 ratio with DABCO) at 25° C. and aged for 4 hours. Slurry was filtered to removing at least 98% of originally charged DABCO from solution. Crude alcohol product can be used directly in subsequent step.

Example 48

Evaluation of the Immobilized Resin Workup Procedure and Demonstration of Immobilized Enzyme Activity in the 90% Organic Solvent System Several immobilization workup procedures were evaluated. The immobilized resins were filtered and washed only with 100 mM potassium phosphate buffer (pH 6.5-7), or with 100 mM potassium phosphate buffer and 10% acetone, or with 100 mM potassium phosphate buffer and 10% 2-propanol, or with 100 mM potassium phosphate buffer and 3% polyethylene glycol (PEG). After wash, the wet immobilized enzyme was dried under vacuum with a nitrogen sweep to remove water from the outer surface of the immobilized enzyme resin. The immobilized preparation was stirred while drying to allow for even moisture content throughout the immobilized enzyme bed and to prevent over- or under-drying any portion of the immobilized enzyme preparation.

20 mg of acetophenone was dissolved 0.9 mL isopropyl alcohol and 0.1 ml water. 100 mg of dried immobilized ketoreductase P1B2 (immobilized on resin IB-150A) was added to the reaction. The reaction was stirred at 30° C. Samples were taken over 1 hour and 20 hours and conversion and ee were determined. The immobilized ketoreductase exhibited reasonable activity as compared to the lyophilized free enzyme. Other organic solvent system with isopropyl alcohol (organic solvent/IPA/water ratio=40/50/10) were also evaluated in immobilized KRED reactions, the organic solvents include toluene, hexanes, methyl tert-butyl ether, Me-THF, IPAc, CPME and DCM. The immobilized ketoreductase exhibited reasonable activity in these 90% organic solvent system.

What is claimed is:

1. An immobilized ketoreductase composition comprising an immobilized resin comprising a recombinant ketoreductase, wherein the recombinant ketoreductase is ketoreductase P1B2, wherein the recombinant ketoreductase is attached to the resin by covalent bonds, wherein the resin is SEPABEADS EXEEC-HFA/S; and a solvent system wherein the solvent system comprises at least 90% organic solvents and wherein the immobilized ketoreductase is stable in the solvent system.

* * * * *

SEQUENCE LISTING

```
<160> NUMBER OF SEQ ID NOS: 1

<210> SEQ ID NO 1
<211> LENGTH: 252
<212> TYPE: PRT
<213> ORGANISM: Artificial Sequence
<220> FEATURE:
<223> OTHER INFORMATION: Engineered variant of Lactobacillus kefir
      ketoreductase

<400> SEQUENCE: 1

Met Thr Asp Arg Leu Lys Gly Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Val
    50                  55                  60

Ser Asp Glu Ala Gly Trp Pro Lys Leu Phe Asp Thr Thr Glu Glu Ala
65                  70                  75                  80

Phe Gly Pro Val Thr Thr Val Val Asn Asn Ala Gly Ile Pro Val Val
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Val
    130                 135                 140

Phe Gly Ile Val Gly Asp Pro Thr Thr Gly Ala Tyr Cys Ala Ser Lys
145                 150                 155                 160
```

-continued

```
Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Met Asp Asp Tyr Glu Gly Ala Glu Glu Met Phe Ser Gln
        195                 200                 205

Arg Thr Lys Thr Pro Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Phe Thr Ala Gln
                245                 250
```